United States Patent
Frey

(10) Patent No.: US 8,404,918 B2
(45) Date of Patent: Mar. 26, 2013

(54) ENERGY EFFICIENCY IN ADSORPTIVE SEPARATION

(75) Inventor: Stanley J. Frey, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 735 days.

(21) Appl. No.: 12/568,228

(22) Filed: Sep. 28, 2009

(65) Prior Publication Data

US 2011/0077448 A1    Mar. 31, 2011

(51) Int. Cl.
*C07C 7/12* (2006.01)
(52) U.S. Cl. .................. 585/826; 585/828; 585/910
(58) Field of Classification Search .................. None
See application file for complete search history.

(56) References Cited

U.S. PATENT DOCUMENTS

| | | | |
|---|---|---|---|
| 4,168,935 | A | 9/1979 | Ueda et al. |
| 4,625,125 | A | 11/1986 | Kuwabara |
| 4,726,744 | A | 2/1988 | Arnold |
| 4,754,156 | A | 6/1988 | Shiozaki et al. |
| 7,208,651 | B2 | 4/2007 | Frey |
| 2005/0198999 | A1* | 9/2005 | Gaskin ............................ 62/625 |
| 2006/0199989 | A1* | 9/2006 | Frey .............................. 585/828 |

* cited by examiner

*Primary Examiner* — Tam M Nguyen
(74) *Attorney, Agent, or Firm* — Mark R Willis

(57) ABSTRACT

The present process comprises a means for energy savings in a process pump by combining the pump with a power-recovery turbine. The invention is particularly useful in the separation of a desired product from a mixture of components using simulated-moving-bed adsorption associated with a large circulating stream with a power-recovery turbine feature for conservation of energy relative to the known art. The improvement is particularly applicable to a process for the separation of para-xylene from mixed $C_8$ aromatics.

15 Claims, 3 Drawing Sheets

ENERGY EFFICIENCY IN ADSORPTIVE SEPARATION

FIELD OF THE INVENTION

The subject invention relates to energy conservation in processes requiring substantial energy requirements for pumping liquids. More specifically, the invention relates to energy recovery in processes for the adsorptive separation of hydrocarbons.

BACKGROUND OF THE INVENTION

The present invention is applied in the context of petroleum and petrochemical processes wherein substantial energy is consumed in the pumping of liquids. Examples of such applications are the pumping of liquid feeds to elevated pressures and recycle processes in which relatively large volumes of liquids are circulated within the process. The invention is particularly relevant wherein the pumping rate is variable, with resulting inefficiency in the energy requirement.

One specific application is in continuous-separation processes for the selective adsorption of an extract from a mixture comprising a raffinate and/or another byproduct. Such processes are in widespread use for the separation of hydrocarbons, for example the separation of para-xylene and/or meta-xylene from a mixture of $C_8$ aromatics, normal paraffins from a paraffin mixture, or specific olefins from a mixture of olefins and paraffins. Generally, the processes use a solid adsorbent which preferentially retains the extract in order to separate the extract from the rest of the mixture.

The solid adsorbent often is in the form of a simulated moving bed, wherein the bed of solid adsorbent is held stationary and the locations at which the various streams enter and leave the bed are periodically moved. The adsorbent bed itself is usually a succession of fixed sub-beds. The shift in the locations of liquid input and output in the direction of the fluid flow through the bed simulates the movement of the solid adsorbent in the opposite direction. The shift in locations of liquid input and output is accomplished by a fluid directing device known generally as a rotary valve which works in conjunction with distributors located between the adsorbent sub-beds. A circulating stream is conducted by pumps circulating liquid from the bottom to the top of the bed of adsorbent. The composition of the circulating stream changes with each valve step. The bed of adsorbent may be contained in two or more chambers, with corresponding numbers of circulating streams and pumps. The circulating pumps, moving substantial and varying quantities of material around one or multiple adsorbent chambers, are significant energy consumers.

For greater detail regarding the simulated moving bed and its operation, see U.S. Pat. No. 2,985,589. Relevant to a para-xylene separation process; see Mowry, J. R. In Handbook of Petroleum Refining Processes; Meyers, R. A. Ed.; McGraw-Hill: New York, 1986; pp 8-79 to 8-99.

SUMMARY OF THE INVENTION

The purpose of the present invention is to provide energy savings in variable-rate pumping of liquids in petroleum and petrochemical processes. The invention is particularly valuable in mitigating high pumping-energy use in a simulated-moving-bed adsorption process.

A broad embodiment of the invention comprises a process for controlling the flowrate of and recovering energy from a liquid stream in a cycle of processing wherein the pressure of the stream is increased by pumping at a flowrate which varies during the cycle of processing by at least about 10% comprising directing a portion of the pumped liquid stream through one or more variable-load power-recovery turbines.

A more specific embodiment comprises a process for controlling the flowrate of and recovering energy from at least one circulating stream in a process for the separation of a desired compound from a feed stream comprising two or more chemical compounds by adsorptive separation in a simulated moving bed contained in one or more multi-bed adsorbent chambers comprising a plurality of access points, wherein a feed stream and a desorbent stream are injected into and an extract stream comprising the desired compound and a raffinate stream are individually withdrawn from the one or more adsorbent chambers during a cycle of the adsorption through shifting individual access points and the at least one circulating stream comprises varying proportions of feed, desorbent, extract and raffinate pumped through the one or more adsorbent chambers and wherein the pressure of the one or more circulating streams is increased by pumping at a flowrate which varies during the cycle of processing by at least about 10%, comprising directing a portion of the at least one pumped circulating stream through one or more variable-load power-recovery turbines.

A yet more specific embodiment comprises a process for controlling the flowrate of and recovering energy from at least one circulating stream in a process for the separation of para-xylene from mixed $C_8$-aromatics by adsorptive separation in a simulated moving bed contained in one or more multi-bed adsorbent chambers comprising a plurality of access points, wherein the $C_8$-aromatics stream and a desorbent stream are injected into and an extract stream comprising para-xylene and a raffinate stream are individually withdrawn from the one or more adsorbent chambers during a cycle of the adsorption through shifting individual access points, and at least one circulating stream comprising varying proportions of mixed $C_8$-aromatics, desorbent, para-xylene and raffinate is pumped through the one or more adsorbent chambers at a varying flowrate which varies during a cycle of the processing by at least about 10% as determined by the varying proportions and step time of shifting access points, comprising directing a portion of the at least one pumped circulating stream through one or more variable-load power-recovery turbines.

DETAILED DESCRIPTION OF THE INVENTION

As mentioned above, the present invention provides energy savings which are particularly relevant in variable-rate pumping of liquids in petroleum and petrochemical processes. When the flowrate of a pumped liquid stream varies during a cycle of processing by at least about 10%, and especially by about 25% or more, the pressure loss and related energy loss across the flow-controlling valve has a substantial effect on processing costs. Energy may be recovered, preferably in the form of power, by directing a portion of the pumped liquid stream through a variable-load power-recovery turbine.

The invention may be applied in one or more cycles of processing comprising conversion processes such as, for example, reforming, isomerization, hydrogenation, hydrocracking, catalytic cracking, and oxygenation and in separation processes. It is particularly useful in adsorptive separation in which large volumes of liquids are recirculated at variable rates within the process. Control valves to control such liquid flows encounter large pressure drops particularly at relatively low flow rates.

Figure 1:
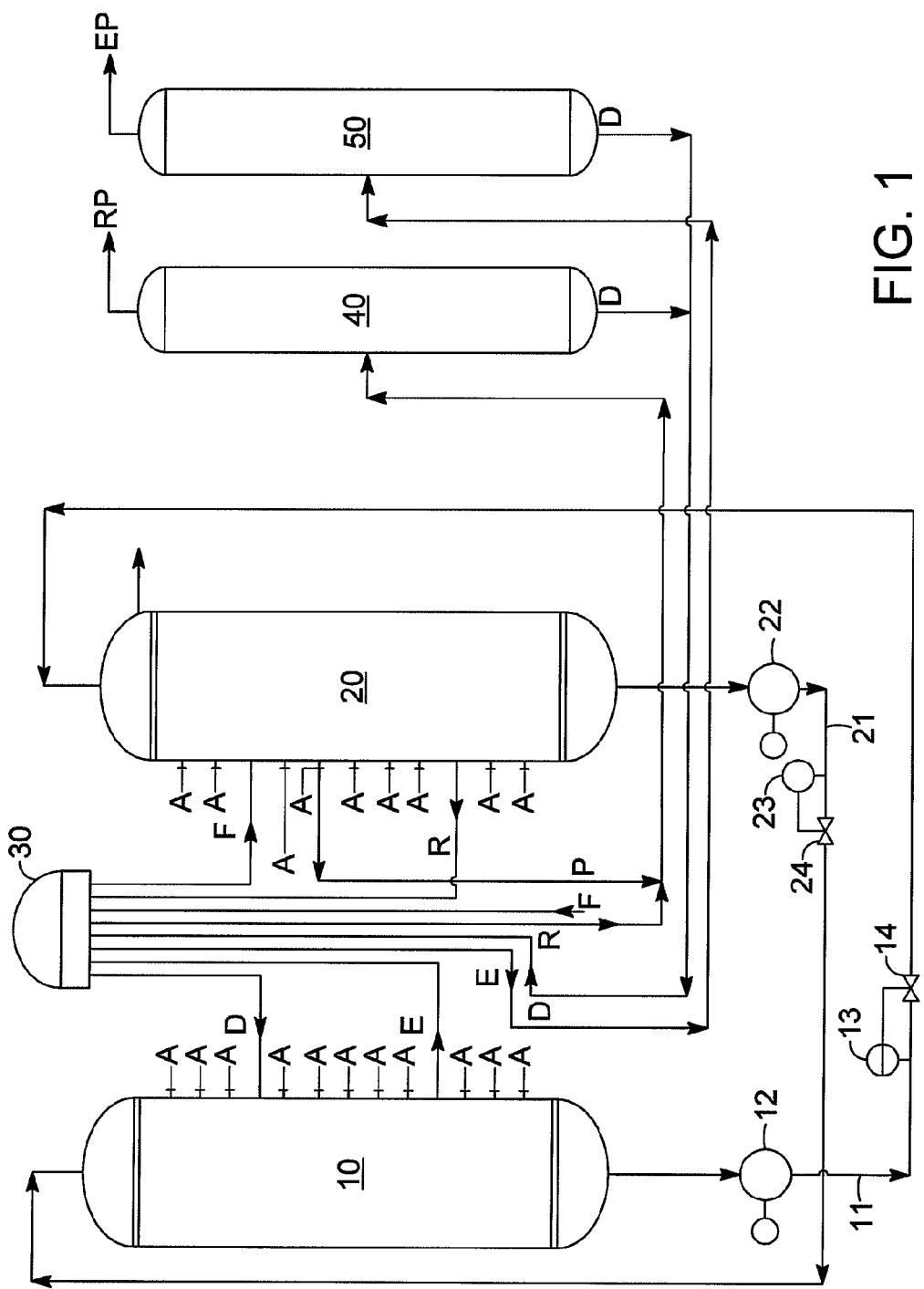
FIG. 1 is a schematic drawing of a conventional simulated-moving bed adsorption process for the recovery of para-xylene from mixed $C_8$ aromatics.

FIG. 1 illustrates the known art in the context of a process for the recovery of para-xylene from mixed $C_8$ aromatics using a solid adsorbent in the form of a simulated moving bed. The bed of solid adsorbent is held stationary and may be contained in two or more chambers 10 and 20. The adsorbent bed itself is usually a succession of fixed sub-beds. The locations at which various streams enter and leave the bed are periodically moved via access points A. The shift in the locations of liquid input and output in the direction of the fluid flow through the bed simulates the movement of the solid adsorbent in the opposite direction. The shift in locations of liquid input and output is accomplished by a fluid directing device 30 known generally as a rotary valve which works in conjunction with distributors located between the adsorbent sub-beds. The rotary valve accomplishes moving the input and output locations to specific distributors via access points A located between the adsorbent sub-beds. After a specified time period, called the step time, the rotary valve advances one index and redirects the liquid inputs and outputs to the distributors immediately adjacent and downstream of the previously used distributors.

The principal liquid inputs and outputs of the adsorbent system consist of four streams: the feed F, the extract E, the raffinate R, and the desorbent D. Each stream flows into or out of the adsorbent system at a particular flow rate, and each flow rate is independently controlled. The feed, when recovering para-xylene from a mixture of $C_8$ aromatics, comprises a mixture of xylenes and ethylbenzene along with small amounts of non-aromatic hydrocarbons. The desorbent introduced to the adsorbent system comprises a liquid capable of displacing feed components from the adsorbent. The extract, which is withdrawn from the adsorbent system, contains the separated para-xylene which was selectively adsorbed by the adsorbent along with desorbent. The raffinate, which is withdrawn from the adsorbent system, contains the other xylene isomers, ethylbenzene, and non-aromatic hydrocarbons which were less selectively absorbed by the adsorbent along with the desorbent. There also may be associated flush streams P which purge distributors of inappropriate materials prior to shifting of access points. The streams pass from the adsorbent beds 10 and 20 to fractionators 40 and 50 for recovery of raffinate product RP and extract product EP, respectively, with recycle of desorbent D to the adsorbent chambers.

A circulating stream represented by 11 and 21 is conducted by pumps 12 and 22, respectively, which circulate liquid from the physical bottom of one adsorbent bed chamber to reenter the physical top of the other adsorbent bed chamber. The composition of the circulating stream, comprising feed, desorbent, extract and raffinate, changes with each valve step. As the four principal streams move through the adsorbent bed, not only the composition but also the volume of the combined stream entering and leaving the adsorbent bed varies significantly; the variation typically is as much as 60% when recovering para-xylene from mixed $C_8$ aromatics. The stream that conducts the effluent 11 from the physical bottom of the first chamber 10 via pump 12 to reenter the physical top of the second chamber 20 is considered as the pumparound stream, and the rate of this stream generally is controlled by a flow controller 13 via valve 14. The stream conducting the effluent 21 from the physical bottom of the second chamber 20 to reenter the physical top of the first chamber 10 is considered as the pusharound stream and generally is controlled by a pressure controller 23 and valve 24.

The pumparound and pusharound pumps, moving substantial and varying quantities of material around the adsorbent chambers, are significant energy consumers. The significant variations in the relatively large circulating combined stream result in substantial inefficiencies in energy use in these circulating pumps which must be oversized to accommodate maximum flow. At a low flow rate of 2000 cubic meters per hour, the pressure drop across the associated control valve could be 350 kPa with 200 kW of dissipated power.

Figure 2:
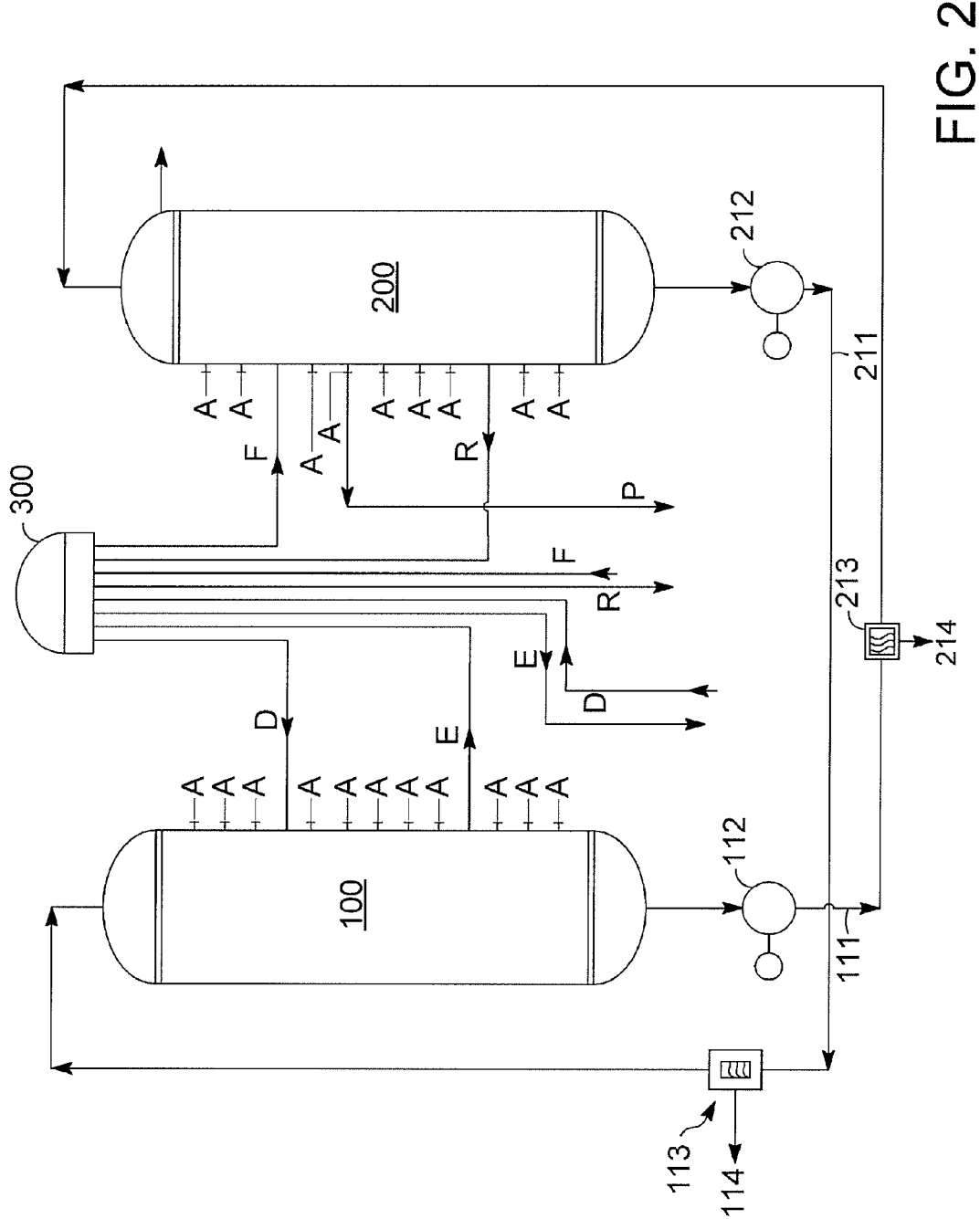
FIG. 2 is a schematic drawing of the FIG. 1 process showing the location of the energy-saving device of the present invention.

To overcome such power losses, the present invention replaces control valves with variable-load power-recovery turbines as shown in FIG. 2. This Figure duplicates the illustration of adsorbent beds 10 and 20 and rotary valve 30 of FIG. 1 with corresponding adsorbent beds 100 and 200 and rotary valve 300; the corresponding fractionators, not involved in the invention, are omitted for simplicity of description. The rate of pumparound stream 111 from adsorbent bed 100 via pump 112 is controlled by varying the inductive load in the power-recovery turbine 113 and optionally adjusting the turbine vanes for maximum turbine efficiency. Correspondingly, the rate of pusharound stream 211 from adsorbent bed 200 via pump 212 is controlled by varying the inductive load in the power-recovery turbine 213 and optionally adjusting the turbine vanes for maximum turbine efficiency. The power-recovery turbines generate electric power per indicators 114 and 214.

Figure 3:
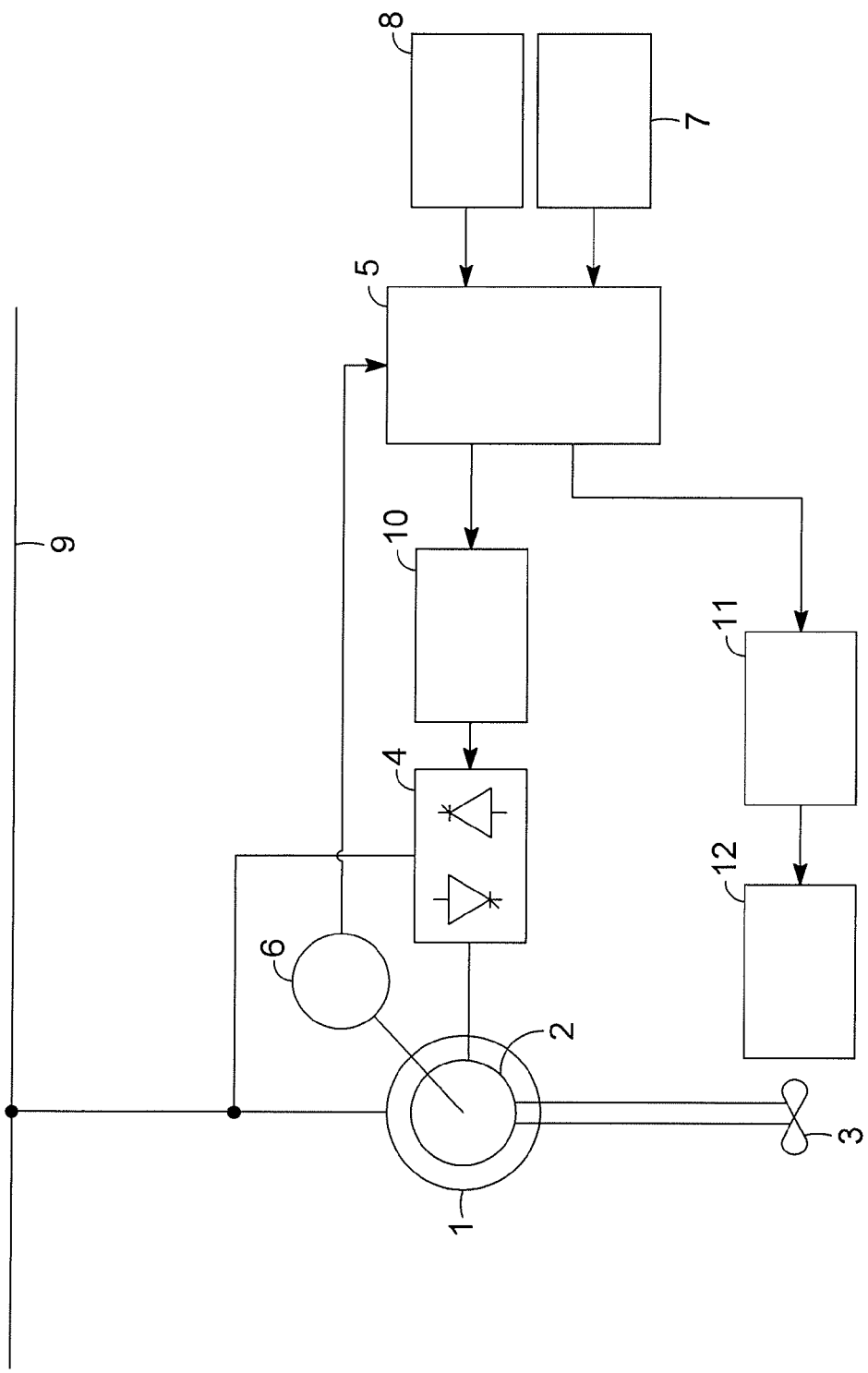
FIG. 3 is a simplified illustration of the energy-saving device of the invention.

To overcome energy losses of the known art, the present invention replaces control valves with variable-load power-recovery turbines. The turbine speed is controlled by one of a variety of means to control and measure the quantity of liquid sent through the pump-turbine combination. FIG. 3 is a schematic illustration of a variable-speed hydraulic power generation system. An induction generator of wound-rotor type 1, having secondary winding 2, is used for this purpose with the rotor thereof coupled with a turbine 3. In accordance with the rotational speed of a generator or generator-motor, an alternating-current of desired frequency is applied to secondary winding thereof to maintain the output frequency thereof at a constant level. The secondary winding 2 is excited by a cycloconverter 4 to effect a variable-speed operation. In the variable-speed operation, a value for the optimum opening of the guide vane is produced by a function generator 5. This function generator 5 determines optimum excitation current and speed in response to outputs from a speed detector 6, a heat detector 7 and an output setting unit 8 in such a manner as to balance effective power and reactive power from a power system 9, thereby controlling the cyclo-converter 4 through an amplifier 10 on one hand and a guide vane 12 through an amplifier 11 connected to a servo motor not shown.

Alternatively, the variable-load power recovery turbine could be calibrated for flow, given the physical constants of the flowing stream, and also be a flow rate indicator eliminating the need for another independent flow rate indicating turbine meter as is now common in the art.

Further details of variable-speed hydraulic generating systems can be found in U.S. Pat. No. 4,625,125; U.S. Pat. No. 4,694,189; and U.S. Pat. No. 4,754,156, incorporated herein by reference thereto.

It must be emphasized that the above description is merely illustrative of a preferred embodiment, and is not intended as an undue limitation on the generally broad scope of the invention. Moreover, while the description is narrow in scope, one skilled in the art will understand how to extrapolate to the broader scope of the invention. For example, the procedure for the simultaneous control of more than one characteristic can be readily extrapolated from the foregoing description. Similarly, one skilled in the art would understand how both the step time and the flow rates of the streams might be adjusted.

The invention claimed is:

1. A process for controlling the flowrate of and recovering energy from a liquid stream in a cycle of processing comprising directing a portion of the liquid stream through one or more variable-load power-recovery turbines to control the flowrate of the liquid stream and generate electric power therefrom, wherein the pressure of the stream is increased by pumping at a flowrate which varies during the cycle of processing by at least about 10%.

2. The process of claim 1 wherein the flowrate is measured and controlled by varying one or more of the speed and output frequency of each of the one or more power-recovery turbines.

3. The process of claim 1 wherein the flowrate varies by about 25% or more.

4. The process of, claim 1 wherein the cycle of processing comprises an adsorptive separation process.

5. A process for controlling the flowrate of and recovering energy from at least one circulating stream in a process comprising separation of a desired compound from a feed stream comprising two or more chemical compounds by adsorptive separation in a simulated moving bed contained in one or more multi-bed adsorbent chambers comprising a plurality of access points, wherein a feed stream and a desorbent stream are injected into and an extract stream comprising the desired compound and a raffinate stream are individually withdrawn from the one or more adsorbent chambers during a cycle of the adsorption through shifting individual access points and the at least one circulating stream comprises varying proportions of feed, desorbent, extract and raffinate pumped through the one or more adsorbent chambers and wherein the pressure of the one or more circulating streams is increased by pumping at a flowrate which varies during the cycle of processing by at least about 10%, comprising directing a portion of the at least one pumped circulating stream through one or more variable-load power-recovery turbines to control the flowrate of the liquid stream and generate electric power therefrom.

6. The process of claim 1 wherein the flowrate is measured and controlled by varying one or more of the speed and output frequency of each of the one or more power-recovery turbines.

7. The process of claim 1 wherein the flowrate varies by about 25% or more.

8. The process of claim 5 wherein the feed stream comprises mixed $C_8$ aromatics and the extract stream comprises para-xylene.

9. The process of claim 5 wherein the feed stream comprises mixed $C_8$ aromatics and the extract stream comprises meta-xylene.

10. The process of claim 5 wherein the feed stream comprises a mixture of aliphatic and aromatic hydrocarbons and the extract stream comprises normal paraffins.

11. The process of claim 5 wherein the feed stream comprises a mixture of paraffinic and olefinic hydrocarbons and the extract stream comprises normal olefins.

12. A process for controlling the flowrate of and recovering energy from at least one circulating stream in a process comprising separation of para-xylene from mixed $C_8$-aromatics by adsorptive separation in a simulated moving bed contained in one or more multi-bed adsorbent chambers comprising a plurality of access points, wherein the $C_8$-aromatics stream and a desorbent stream are injected into and an extract stream comprising para-xylene and a raffinate stream are individually withdrawn from the one or more adsorbent chambers during a cycle of the adsorption through shifting individual access points, and at least one circulating stream comprising varying proportions of mixed $C_8$-aromatics, desorbent, para-xylene and raffinate is pumped through the one or more adsorbent chambers at a varying flowrate which varies during a cycle of the processing by at least about 10% as determined by the varying proportions and step time of shifting access points, comprising directing a portion of the at least one pumped circulating stream through one or more variable-load power-recovery turbines to control the flowrate of the liquid stream and generate electric power therefrom.

13. The process of claim 12 wherein the flowrate is measured and controlled by varying one or more of the speed and output frequency of each of the one or more power-recovery turbines.

14. The process of claim 12 wherein the at least one circulating stream comprises one or more pumparound streams and one or more pusharound streams.

15. The process of claim 12 wherein the flowrate varies by about 25% or more.

* * * * *